United States Patent
Fitzpatrick et al.

(10) Patent No.: US 7,132,446 B1
(45) Date of Patent: **\*Nov. 7, 2006**

(54) ISOLATION OF A DIMER DI-GALLATE, A POTENT ENDOTHELIUM-DEPENDENT VASORELAXING COMPOUND

(75) Inventors: David F. Fitzpatrick, Tampa, FL (US); Rebecca O'Malley, Tampa, FL (US)

(73) Assignee: University of South Florida, Tampa, FL (US)

( * ) Notice: Subject to any disclaimer, the term of this patent is extended or adjusted under 35 U.S.C. 154(b) by 391 days.

This patent is subject to a terminal disclaimer.

(21) Appl. No.: 10/605,787

(22) Filed: Oct. 27, 2003

Related U.S. Application Data

(63) Continuation-in-part of application No. 10/065,770, filed on Nov. 18, 2002, now Pat. No. 6,706,756.

(60) Provisional application No. 60/332,428, filed on Nov. 16, 2001.

(51) Int. Cl.
*A61K 31/35* (2006.01)

(52) U.S. Cl. ..................................................... 514/456

(58) Field of Classification Search ................. 514/456
See application file for complete search history.

(56) References Cited

U.S. PATENT DOCUMENTS 6,706,756 B1 * 3/2004 Fitzpatrick ................. 514/456

OTHER PUBLICATIONS

Yoshmura et al.; Evaluation of the NO Scavenging Activity of Procyanidin in Grape Seed by use of the TMA-PTIO/NOC 7 ESR System; Journal of Agricultural & Food Chemistry; 2003.
Fisher et al.; Flavanol-rich Coca Induces Nitric-Oxide-Dependent Vasodilation in Healthy Humans; Journal of Hypertension; vol. 21, No. 12; 2003.

* cited by examiner

*Primary Examiner*—Amelia A. Owens
(74) *Attorney, Agent, or Firm*—Thomas E. Toner; Smith & Hopen, P.A.

(57) ABSTRACT

Certain proanthocyanidins found in various wines, grape juice, and other plant extracts exhibit endothelium-dependent vasorelaxing activity that involves increased nitric oxide production by endothelial cells. The smallest procyanidins (PCs) possessing substantial EDR activity were isolated from grape seeds. A dimer di-gallate (epicatechin-galloyl-epicatechin-gallate) was purified from concord grape seed extracts by Toyopearl TSK-40 gel chromatography, HPLC and electrospray FTMS. Further characterization was achieved using tannase treatment and acid thiolysis. This compound had an EC50 for vasorelaxation of $0.67 \pm 0.04$ μg/ml when tested for endothelium-dependent relaxing activity in phenylephrine pre-contracted rat aortic rings.

8 Claims, 7 Drawing Sheets

(A)

(B)

ISOLATION OF A DIMER DI-GALLATE, A POTENT ENDOTHELIUM-DEPENDENT VASORELAXING COMPOUND

CROSS-REFERENCE TO RELATED APPLICATIONS

This application is a continuation-in-part of U.S. application Ser. No. 10/065,770 filed Nov. 18, 2002 now U.S. Pat. No. 6,706,756, which claimed priority to U.S. Provisional Application No. 60/332,428 filed Nov. 16, 2001. The disclosures of which are hereby incorporated by reference in their entireties.

BACKGROUND OF INVENTION

FIELD OF INVENTION

This invention relates to compounds that demonstrate anti-oxidant and vascular properties, including endothelium-dependent relaxation in blood vessels.

BACKGROUND OF THE INVENTION

Some red wines, grape juices, and many other extracts of commonly consumed food plants (fruits, vegetables, nuts, spices) have been shown to cause endothelium-dependent relaxation (EDR) of blood vessels in vitro. This EDR activity results from enhanced nitric oxide (NO) production by endothelial cells, and subsequent stimulation of cyclic GMP in the vascular smooth muscle target tissue. The vascular NO-cyclic GMP pathway is important in a number of vaso-protective mechanisms in addition to vasodilation, e.g., inhibition of platelet aggregation, inhibition of platelet and neutrophil adhesion to endothelium, and inhibition of low-density lipoprotein (LDL) oxidation. Thus, there appear to be compounds present in edible plants and extracts and beverages prepared from them, which may aid in preventing and possibly halting progression of cardiovascular diseases, and perhaps enhancing sexual function, much as do selective phosphodiesterase inhibitors such as sildenafil.

The compounds responsible for EDR activity have been under investigation in this laboratory and others. Flavanoid monomers are generally either inactive or require high concentrations for EDR activity, although leucocyanidol and delphinidin have some activity at lower concentrations. In a previous study, the inventors showed that much of the EDR activity of grape seed extracts was most likely due to the procyanidin (PC) content. PCs are oligomers and polymers composed of (+)-catechin and (−)-epicatechin units attached to each other, usually by (4→8) linkages, but sometimes by (4→6) linkages. Some PCs are esterified, usually by gallic acid. EDR activity appears to be related to (1) molecular size (larger PCs are more active, in general, than smaller ones); (2) epicatechin:catechin ratio (PCs with a preponderance of epicatechin are generally more active); (3) degree of galloylation (galloylation seems to increase activity for a compound of given size and catechin/epicatechin content).

The objective of the study which led to the inventor's discovery disclosed herein was to isolate and identify the smallest PC possessing characteristics (2) and (3) above, and to test its EDR activity. This compound, a dimer composed of two galloylated epicatechins, has been successfully purified and found to be highly EDR-active.

SUMMARY OF INVENTION

The present invention is an isolated compound and method of inducing endothelium-dependent relaxation in blood vessels including the step of introducing isolated procyanidins having two or moref (−)-epicatechins to a patient wherein the procyanidins are galloylated. To achieve both bioavailability and potency the number of epicatechin monomers forming each procyanidin is two, with each monomer being galloylated. Specifically, epicatechin-galloyl-epicatechin-gallate (B2-di-gallate), a dimer including two epicatechin gallates, is administered to a patient. To reverse the relaxation of the blood vessels, a NO synthase inhibitor may be used. To enhance endothelium-dependent relaxation, a concomitant administration of L-arginine may be performed.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
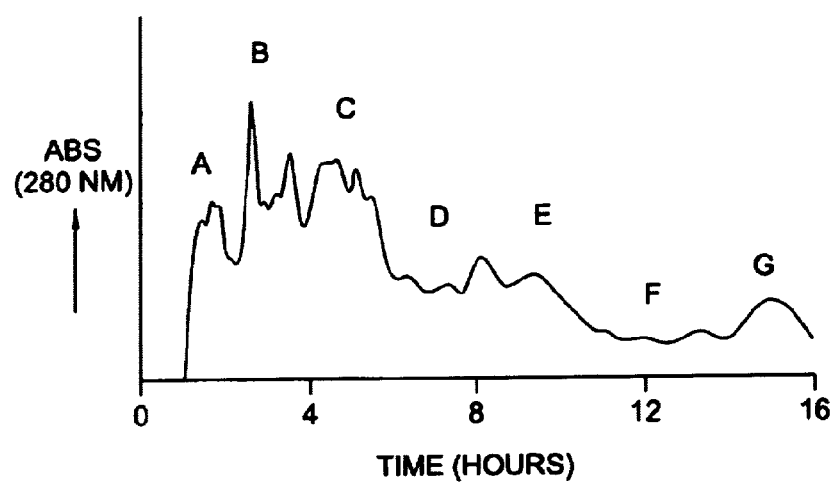
FIG. 1 is a Toyopearl TSK HW(40) elution profile of grape seed extract eluted with methanol; absorbance measured at 280 nm.

Grape seed extraction and preliminary fractionation. Extraction and preliminary Toyopearl separation of seeds was performed essentially as described previously. Briefly, Concord grape seeds (provided by Welch Foods, Inc., Concord, Mass.) were crushed and extracted into methanol (100 ml/25 gms. of seeds for 30 min.×3), concentrated, filtered, then applied to a column (35×2.5 cm, i.d.) of Toyopearl TSK HW-40 resin. Elution was carried out with methanol. Seven fractions were collected, evaporated, and redissolved in water (for EDR testing, HPLC analysis and tannase treatment) or methanol (for mass spectrometry and acid thiolysis).

HPLC. A Waters HPLC system was employed and consisted of a U6K injector, two 510 pumps, and a 481 UV/Vis detector, in conjunction with a Waters μBondapak C18 column (3.9×300 mm), protected by a guard column of the same material. The gradient solutions consisted of: Mobile phase A 2.5% acetic acid; Mobile phase B 40% acetonitrile in A. For most analytical runs, the gradient ran from 25% B to 50% B in 30 min; from 50% B to 100% B during 30 to 35 min; isocratic at 100% B during 35 to 40 min. Finally the gradient was brought back to 100% A to prepare for the next run. For analysis of thiolysis products the same solutions were employed, and the gradient used was: 35% B to 50% B in 20 min; from 50% B to 100% B during 20 to 25 min; isocratic at 100% B from 25 to 45 min; then back to 100% A to prepare for the next run. For all HPLC runs, flow rate was 0.7 mL/min and detection was made at 280 nm.

Electrospray-mass spectrometry. Fractions eluted from the Toyopearl column and individual peaks were examined by mass spectrometry using a 7 Tesla FTMS (Fourier Transform Mass Spectometer) (ion Spec Corp., Lake Forest, Calif.) equipped with an off-axis electrospray ionization source (Analytica, Bradford, Conn.). Spectra were obtained in both the positive and negative ion modes. For detailed characterization of the dimer di-gallate MS/MS experiments were performed. The electrospray matrix was 80% MeOH: 20% $H_2O$ for both positive and negative ion spectra. A Cole-Palmer infusion pump was used to deliver the samples continuously to the source with a flow rate of 25 μL/hr.

Chemical analyses. For determining whether or not EDR-active PCs were galloylated, purified samples in water were incubated with tannase (Juelich Fine Chemicals, Juelich, Germany) at 35° for varying lengths of time, followed by HPLC analysis of the products. The thiolytic degradation method was based on the method of Rigaud et al. Purified PC sample in methanol was incubated with an equal amount of benzyl mercaptan solution (12% benzyl mercaptan in 0.4 M HCl, made up in methanol) at 50° for varying lengths of time, followed by HPLC analysis of the products.

Aortic ring preparation and bioassay. The procedure for preparation of rat aortic rings and general aspects of determining mechanical activity has been previously described. Briefly, male Sprague-Dawley rats (200–225 g) were euthanized with an overdose of sodium pentobarbital (100 mg/kg, i.p.), bled, and the thoracic aorta excised, cleaned, and rings (3–4 mm in length) were cut, taking care not to disturb the endothelium. In some instances the endothelium was deliberately removed by gently rubbing the lumen with a curved forceps. The rings were suspended in tissue baths containing a physiologic salt solution (PSS) with the following composition (in millimolar): 118 NaCl; 4.7 KCl; 25 $NaHCO_3$; 1.2 $MgSO_4$; 1.2 $NaH_2PO_4$; 0.026 EDTA; 1.5 $CaCl_2$; 11 glucose. The solution was bubbled continuously with $O_2/CO_2$ (95%/5%), and maintained at 37° C. Activity was recorded on a Grass polygraph. After equilibration for at least 1 hr under 1.5 g of tension, tissues were contracted submaximally (approximately 80% of Emax) with phenylephrine (~1 μM), and then 3 μM acetylcholine, a known EDR-active compound, was added to the bath to test for intactness of the endothelium. Rings were washed with PSS three times over the next 45 min. prior to the next sequence.

EDR activity of HPLC peaks was determined by first contracting aortic rings with phenylephrine, as above, then generating concentration-response curves for relaxation by adding each peak sample to the bath, beginning with a sub-threshold concentration and adding increasing amounts until maximum relaxation is achieved. To test for endothelium-dependence, denuded aortic rings were used. Successful endothelium removal was established by a lack of relaxation response to 3 μM acetylcholine. The peak material did not exhibit any relaxing activity using de-endothelialized rings.

Statistical methods. Data are presented as means±SEM. EC50s were determined from concentration-response curves, utilizing nonlinear regression analysis software (GraphPad Prizm, San Diego, Calif.).

RESULTS AND DISCUSSION

Toyopearl Fractionation. Toyopearl TSK HW-405 fractionation of grape seed extracts yielded 7 fractions, labeled A through G (FIG. 1). Compounds found in the earlier (A–C) fractions (phenolic acids, catechin, epicatechin, and epicatechin gallate) were easily identified by their co-elution with available standards. These fractions exhibited very little EDR activity when bioassayed, whereas the remaining Toyopearl fractions containing PCs displayed varying degrees of vasorelaxing potency and efficacy, as described previously (11) and incorporated herein by reference in its entirety.

Figure 2:
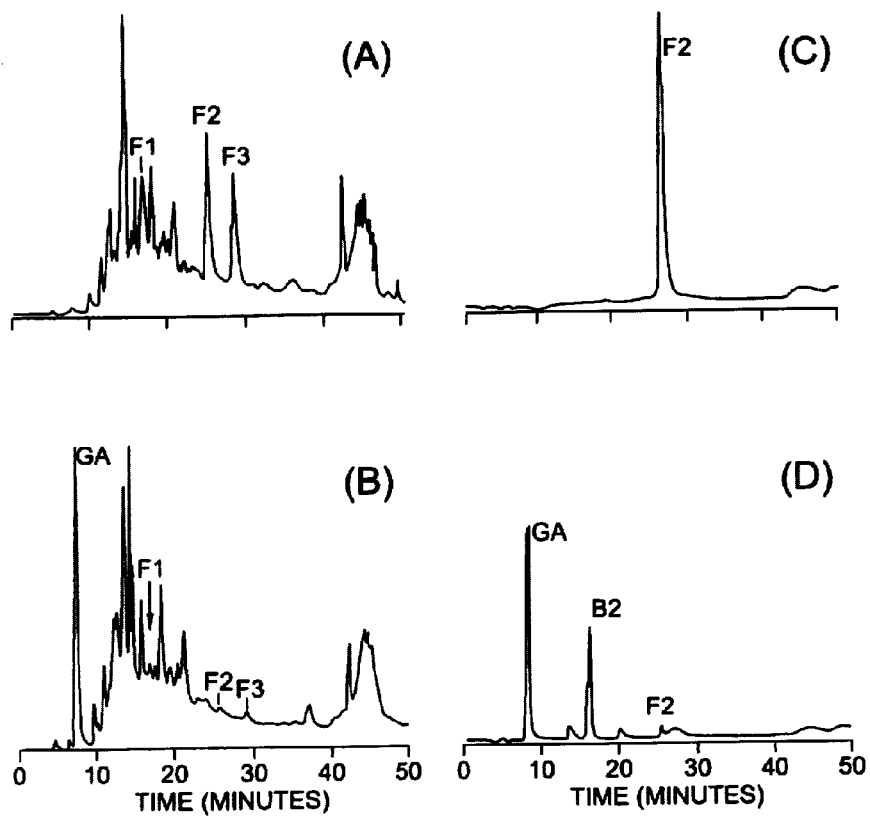
FIG. 2 is a HPLC of Fraction F from Toyopearl elution before (a) and after (b) tannase treatment, and Peak F2 before (c) and after (d) tannase treatment. Tannase treatment virtually eliminates galloylated proanthocyanidin peaks, yielding gallic acid (GA) and non-galloylated proanthocyanidins, e.g. B2 dimer in (d).

Determination of galloylated compounds in Toyopearl fractions. In the search for the Toyopearl fraction containing B2-di-gallate, the galloylated compounds in selected fractions were determined by running a sample of a given fraction on HPLC before and after tannase treatment, and comparing the chromatograms. Missing or much reduced peaks following tannase treatment indicated galloylated compounds. Based on the results of de Freitas et al., who found B2-di-gallate in a fraction that appeared to most closely correspond to our fraction F, the inventors analyzed this fraction for the compound in question. HPLC chromatograms of Toyopearl fraction F before (FIG. 2(a)) and after (FIG. 2(b)) tannase treatment revealed that three major peaks were gallates, designated F1, F2, and F3. Semi-preparative isolation of these three peaks was undertaken in order to obtain sufficient quantities for subsequent analyses. Treatment of isolated peak compounds F1 and F3 with tannase yielded gallic acid plus peaks that were not consistent with a dimer di-gallate. Tannase treatment of F2 (FIG. 2(c)) however, yielded gallic acid plus a compound that co-eluted with dimer B2 on HPLC (FIG. 2(d)), suggesting that the compound is either a dimer di-gallate or a mono-galloylated dimer compound.

Figure 3:
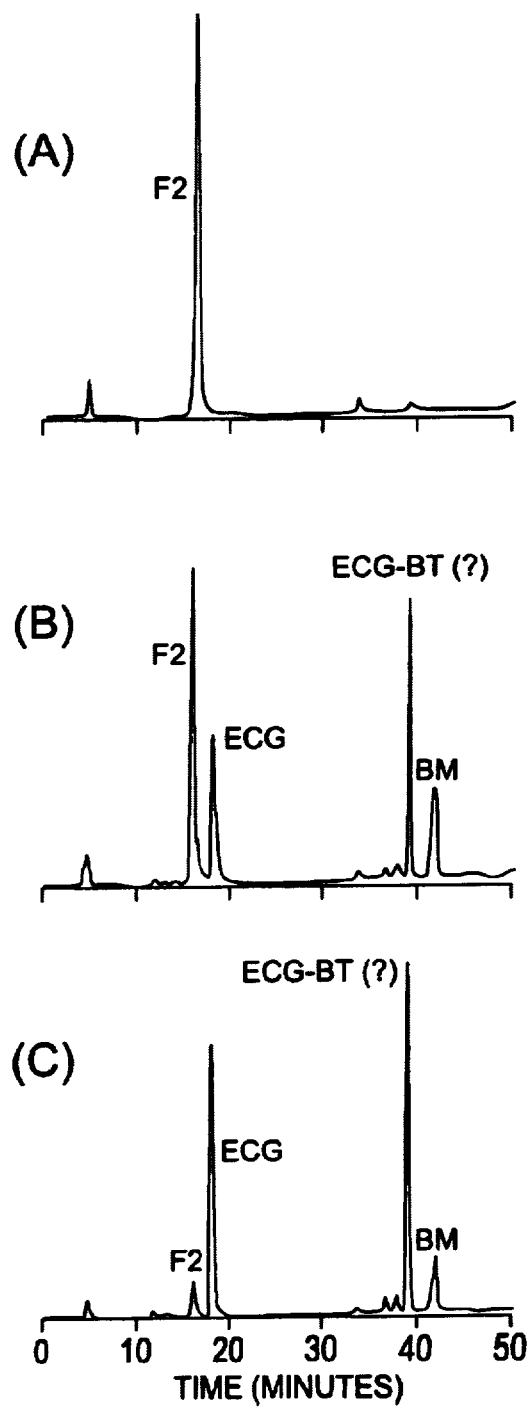
FIG. 3 is a HPLC of Peak F2 before (a), and after 2 min incubation (b), and after 15 min incubation (c) with benzylmercaptan at 50° C. ECG=epicatechin gallate; ECG-BT=epicatechin gallate-benzylthioether; BM=benzylmercaptan.

Thiolytic degradation of HPLC peak compounds. The three galloylated HPLC peak substances of Toyopearl fraction F were subjected to acid thiolysis in order to determine the composition of the compounds. HPLC of thiolytic degradation products of compounds F1 and F3 yielded products inconsistent with the structure of a dimer di-gallate (not shown). Peak F2 (FIG. 3(a)), on the other hand, yielded two products (FIGS. 3(b) and (c)), one which co-eluted with epicatechin-gallate on HPLC, and the other which eluted much later in the run, with a retention time consistent with that of a thioether product.

Figure 4:
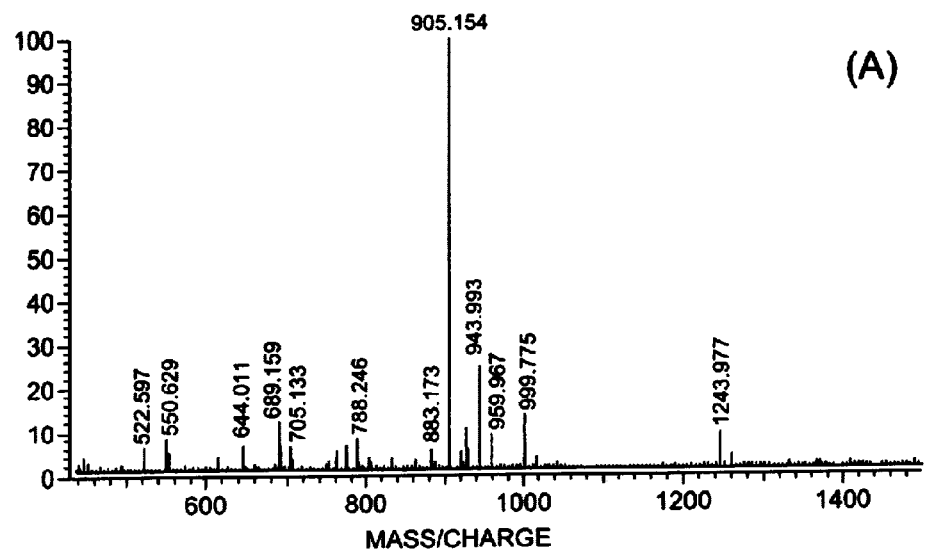
FIG. 4 (a) ES-FTMS in the positive ion mode of the HPLC peak F2 showing molecular ion at m/z=905 (M+Na)$^+$; (b) MS/MS spectrum of (M+Na)$^+$ in positive ion mode.
Figure 4:
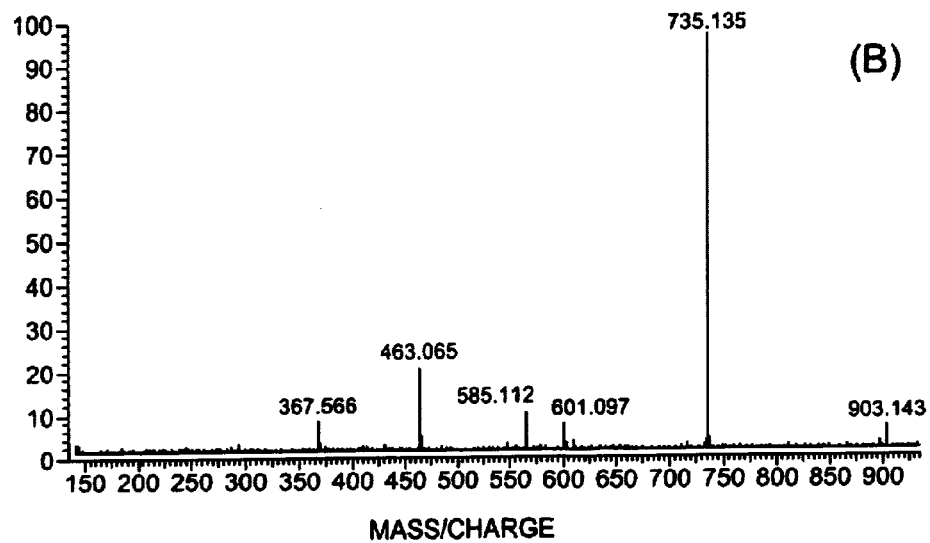
Figure 6:
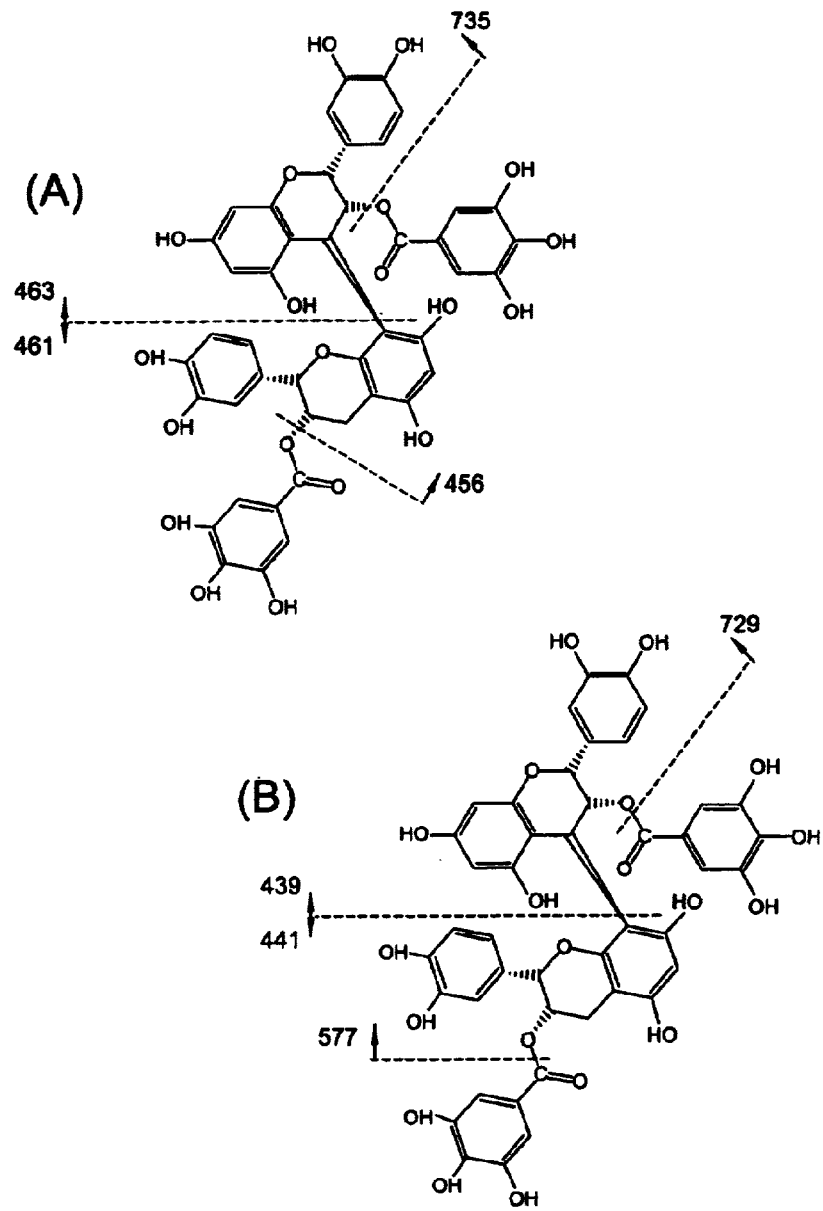
FIG. 6 is a depiction of the sructure of the dimer di-gallate (epicatechin-galloyl-epicatechin-gallate) showing: (a) major fragments of the (M+Na)$^+$ ion observed in the positive ion mode: (b) major fragments of the (M−H)$^-$ ion observed in the negative ion mode.

Mass spectrometry of peak F2. Positive Ion Mode: FIG. 4(a) shows the ES-FTICR MS in positive ion mode. The molecular ion is observed at m/z=905. This corresponds to the $Na^+$ attached ion of a-di-catechin/epicatechin di-gallate (molar mass 882). FIG. 4(b) shows the MS/MS spectrum of m/z=905. Three main fragments are observed at m/z values of 735, 565 and 463, respectively. FIG. 6(a) shows the proposed fragmentation points leading to the observed ions. In the positive ion mass spectra of this type of compound, breaking of the interflavanoid bond, with retention of charge on the upper unit usually leads to an ion corresponding to (upper monomer unit 2H). The observation of the ion at m/z=463 indicates definitively a catechin/epicatechin gallate upper unit in the dimer. Loss of a gallic acid group, probably involving the transfer of a hydrogen atom as shown (fragmentation 1) gives rise to the ion at m/z=735. Loss of a second gallic acid group, again involving the transfer of a hydrogen atom (fragmentation 2) gives rise to the ion at m/z=565. These three observations taken together indicate clearly two gallic acid groups in the molecule, with one of the groups definitely being on the upper monomer unit.

Figure 5:
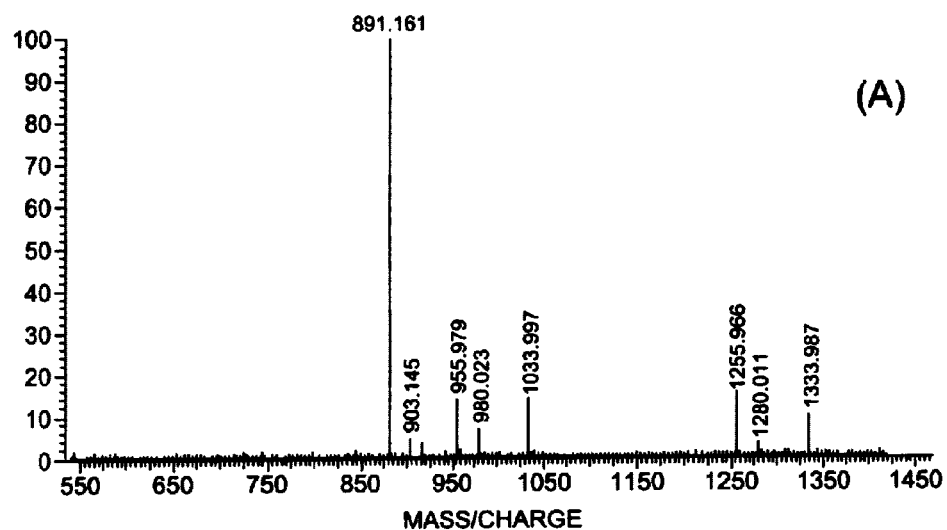
FIG. 5 (a) ES-FTMS in the negative ion mode of the HPLC peak F2 showing molecular ion at m/z=881 (M−H)$^-$; (b) MS/MS spectrum of (M−H)$^-$ in negative ion mode.
Figure 5:
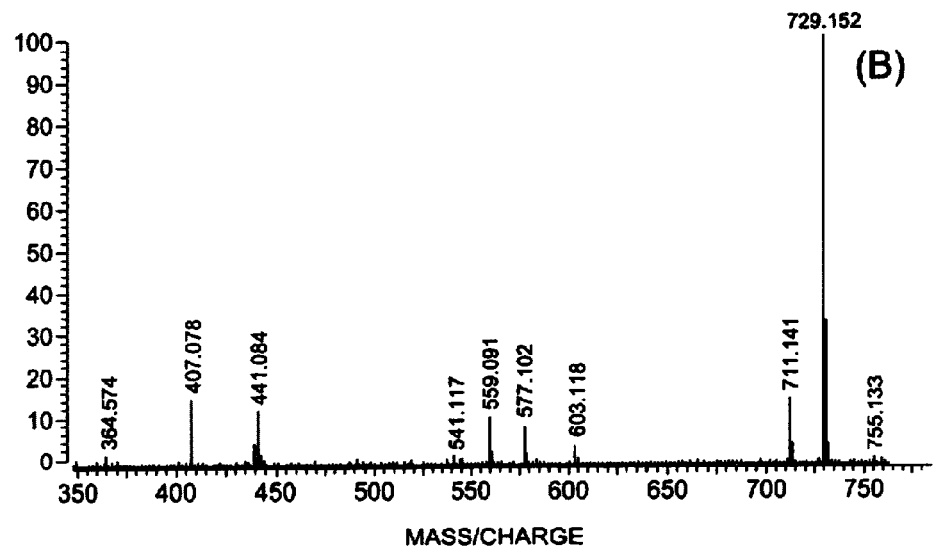

Negative Ion Mode: FIG. 5(a) shows the ES-FTICR MS in negative ion mode. The molecular ion is observed at m/z=881 (M–H)⁻. FIG. 5(b) shows the MS/MS spectrum of m/z=881. Significant fragment ions are observed at m/z=729, 577 and 439, respectively. FIG. 6(b) shows the proposed fragmentation points for the molecule on the negative ion mode. Cleavage of the interflavanoid bond with the charge remaining on the upper unit would be expected to lead to an ion at m/z=439, and cleavage of the interflavonoid bond with retention of charge on the bottom unit would be expected to lead to an ion at m/z=441. Close examination of FIG. 5(b) shows that both m/z=439 and m/z=441 ions are present indicating that both the upper unit and the lower unit in the dimer are catechin/epicatechin gallates.

Loss of part of the gallic acid group ($C_7H_4O_4$) leads to an ion at m/z=729. In this case the oxygen atom bonded to the monomer unit stays attached, leading to a catechin-like structure. The ion at m/z=577 corresponds to a second loss of ($C_7H_4O_4$) (fragmentation 2) or, it could correspond to a Retro-Diels Alder (RDA) fragmentation from the ion having already lost one $C_7H_4O_4$ unit.

Conclusions from Mass Spectrometric Data: The positive and negative data taken together indicate that the substance isolated in the peak F2 has a molar mass of 882, contains two gallate groups and consists of both an upper unit and a lower unit which are catechin/epicatechin gallates. It is not possible from the mass spectrometric data to draw any conclusions about the stereochemistry of the two flavanoid subunits or about the stereochemistry of the linkage between the two units.

Figure 7:
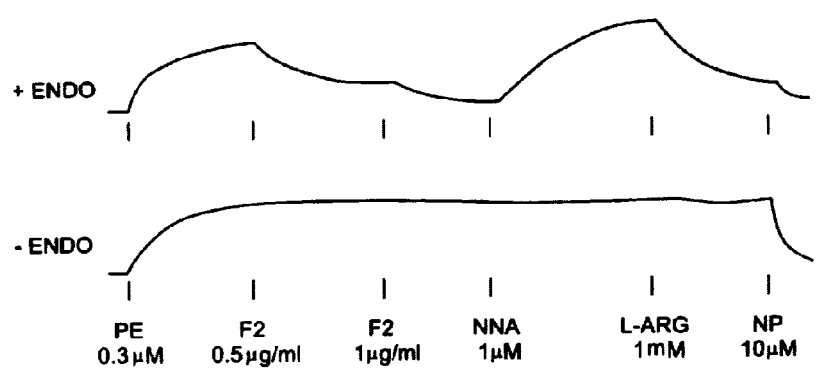
FIG. 7 shows edothelium-dependent relaxing (EDR) activity of Peak F2 (B2-di-gallate). Vertical lines indicate where additions were made to the bath.

EDR activity of B2-di-gallate. Purified peak F2 (B2-di-gallate) relaxed phenylephrine-contracted endothelium-intact rat aortic rings, but had no effect on endothelium-denuded rings (FIG. 7). The relaxation of intact rings was reversed by addition of N-nitro-L-arginine (NNA), a Nitric oxide (NO) synthase inhibitor. L-arginine, the normal substrate for NO synthase, by competing with NNA, caused the tissue to relax once again. Concentration-response curves for relaxation of intact aortic rings yielded an EC50 of 0.67±0.04 μg/ml (0.76 μM); n=4 rats (3–6 concentration-response curves/rat aorta), with a threshold concentration (for 10% relaxation) of approximately 0.35 μg/ml (0.4 μM).

CONCLUSIONS

In the present study, the smallest PCs possessing substantial EDR activity were isolated from grape seeds. Previous studies showed that dimers and trimers per se exhibited low EDR activity, but that galloylation appeared to increase the activity of a given sized compound, as did the ratio of epicatechin:catechin subunits in the molecule. It was determined therefore that the PC most likely to possess these qualities would be B2-di-gallate, a dimer consisting of two epicatechin gallates connected by a (4→8) linkage.

Isolation of the dimer digallate required, first of all, separation of the oligomeric PCs from phenolic acids, monomeric (catechin and epicatechin) flavanols and high molecular weight polymers, by Toyopearl chromatography, followed by tannase treatment of the various PC fractions suspected of containing the desired galloylated compound. Based on retention time and order of elution from Toyopearl (Fractogel) chromatography reported by others, fraction F was examined and found by HPLC to contain three prominent tannase-reactive peaks (peaks eliminated by tannase treatment). Acid-catalyzed thiolysis of the compounds present in these peaks yielded information suggestive of their identity. During acid thiolysis the linkage(s) between subunits of PCs are cleaved, releasing the lower (terminal) subunit in the free state, while the 4-flavanyl carbocation formed from the upper (extension) subunit is captured by the nucleophile, benzylmeacaptan, to yield 4-flavanylbenzyl thioethers. Analysis of the products of this reaction (either as such or following desulfuration) by HPLC, ES-ITMS, etc. is helpful in establishing the identity of proanthocyanidins. Applying this technique, peak F2 was found to yield epicatechin gallate and an unidentified thioether derivative. Based on HPLC of similar thiolytic products of other PC compounds, the thioether derivative was presumed to be epicatechin gallate-benzylthioether.

ES-FTIC MS confirmed the identity of peak F2 as a dimer digallate with molecular weight=882 Daltons. MS/MS data on the pseudo molecular ions in the positive and negative modes indicate clearly that the dimer contains two catechin/ epicatechin units plus two gallate groups. The mass spectrometric data indicates clearly that there is one gallate group on the upper unit and one on the lower unit. The mass spectrometric data does not give any indication of whether the monomer units within the dimer are catechin or epicatechin. However, the thiolysis data shows definitively that the lower unit is epicatechin gallate, and with the lack of observation of any catechin gallate from the extended thiolysis experiment, therefore the isolated procyanidin is indeed epicatechin-galloyl-epicatechin-gallate. This conclusion is supported by finding that a major product following tannase treatment is an HPLC peak that elutes identically to dimer B2 (epicatchin-epcatechin).

The purified dimer digallate was shown to have substantial EDR activity, with the threshold for relaxation and EC50 in the sub-micromolar range. Approximately 0.44 mg of the compound were extracted from 25 gm of seeds. However, because its synthesis has been accomplished, it is now possible to produce it in quantities suitable for incorporation into milligram-quantity oral preparations for in vivo application.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin EW [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of the digallate compounds are administered and dosed in accordance with good medical practice, taking into account the clinical condition of the individual patient, the site and method of administration, scheduling of administration, patient age, sex, body weight, and other factors known to medical practitioners. The pharmaceutically "effective amount" for purposes herein is thus determined by such considerations as are known in the art.

A therapeutically effective amount of B-2 digallate is that amount necessary to provide a therapeutically effective amount of the corresponding procyanidin in vivo. The amount of B-2 digallate must be effective to achieve a response, including but not limited to total prevention of (e.g., protection against) and to improved survival rate or more rapid recovery, or improvement or elimination of symptoms associated with of endothelium-dependent relaxation (EDR) of blood vessels indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

The invention claimed is:

1. A method of inducing endothelium-dependent relaxation in blood vessels comprising introducing an effective amount of epicatechin-galloyl-epicatechin-gallate (B2-digallate) to a patient.

2. The method of claim 1 further comprising the step of concomitantly administering an effective amount of L-arginine to the patient.

3. A pharmaceutical compound for inducing endothelium-dependent relaxation in blood vessels comprising an effective amount of epicatechin-galloyl-epicatechin-gallate (B2-di-gallate).

4. The pharmaceutical compound of claim 3 wherein the epicatechin monomers are galloylated.

5. The pharmaceutical compound of claim 3 further comprising an effective amount of L-arginine.

6. The pharmaceutical compound of claim 3 wherein said compound is selected from the group consisting of dimer di-gallate in the positive ion mode and dimer di-gallate in the negative ion mode.

7. A kit for inducing endothelium-dependent relaxation in blood vessels comprising an effective amount of epicatechin-galloyl-epicatechin-gallate (B2-di-gallate) and an effective amount of L-arginine.

8. The kit of claim 7 wherein said epicatechin-galloyl-epicatechin-gallate is selected from the group consisting of dimer di-gallate in the positive ion mode and dimer di-gallate in the negative ion mode.

* * * * *